US007276330B2

(12) United States Patent
Chow et al.

(10) Patent No.: US 7,276,330 B2
(45) Date of Patent: Oct. 2, 2007

(54) DEVICES, SYSTEMS AND METHODS FOR TIME DOMAIN MULTIPLEXING OF REAGENTS

(75) Inventors: Calvin Y. H. Chow, Portola Valley, CA (US); J. Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 10/418,008

(22) Filed: Apr. 17, 2003

(65) Prior Publication Data

US 2003/0215863 A1 Nov. 20, 2003

Related U.S. Application Data

(62) Division of application No. 09/238,467, filed on Jan. 28, 1999, now abandoned.

(51) Int. Cl.
*C12Q 1/00* (2006.01)

(52) U.S. Cl. ........................................................ 435/4

(58) Field of Classification Search .................... 435/4, 435/6–7.2, 287.1–2; 436/501–526; 422/50, 422/68.1, 108; 204/193–4, 400, 403, 451–3, 204/601, 604; 417/413.1, 207, 412
See application file for complete search history.

(56) References Cited

U.S. PATENT DOCUMENTS

| | | | | |
|---|---|---|---|---|
| 4,390,403 | A | 6/1983 | Batchelder | |
| 4,492,752 | A * | 1/1985 | Hoffman et al. | 435/7.21 |
| 4,735,081 | A * | 4/1988 | Luoma et al. | 73/24.06 |
| 4,908,112 | A | 3/1990 | Pace | |
| 5,126,022 | A | 6/1992 | Soane et al. | |
| 5,180,480 | A | 1/1993 | Manz | |
| 5,223,219 | A | 6/1993 | Subramanian et al. | |
| 5,496,697 | A * | 3/1996 | Parce et al. | 435/5 |
| 5,498,392 | A | 3/1996 | Wilding et al. | |
| 5,571,410 | A | 11/1996 | Swedberg et al. | |
| 5,585,069 | A | 12/1996 | Zanzucchi et al. | |
| 5,593,838 | A | 1/1997 | Zanzucchi et al. | |
| 5,599,432 | A | 2/1997 | Manz et al. | |
| 5,603,351 | A | 2/1997 | Cherukuri et al. | |
| 5,618,494 | A | 4/1997 | Bunce | |
| 5,635,358 | A | 6/1997 | Wilding et al. | |
| 5,637,469 | A | 6/1997 | Wilding et al. | |
| 5,699,157 | A | 12/1997 | Parce | |
| 5,725,363 | A * | 3/1998 | Bustgens et al. | 417/413.1 |
| 5,726,026 | A | 3/1998 | Wilding et al. | |
| 5,750,015 | A | 5/1998 | Soane et al. | |
| 5,779,868 | A | 7/1998 | Parce et al. | |
| 5,800,690 | A | 9/1998 | Chow et al. | |
| 5,842,787 | A | 12/1998 | Kopf-Sill et al. | |
| 5,852,495 | A | 12/1998 | Parce | |
| 5,858,195 | A | 1/1999 | Ramsey | |
| 5,869,004 | A | 2/1999 | Parce et al. | |
| 5,876,675 | A | 3/1999 | Kennedy | |
| 5,880,071 | A | 3/1999 | Parce et al. | |
| 5,882,465 | A | 3/1999 | McReynolds | |
| 5,885,470 | A | 3/1999 | Parce et al. | |
| 5,922,591 | A * | 7/1999 | Anderson et al. | 435/287.2 |
| 5,942,443 | A * | 8/1999 | Parce et al. | 436/514 |
| 5,948,227 | A | 9/1999 | Dubrow | |
| 5,976,336 | A | 11/1999 | Dubrow et al. | |
| 6,030,581 | A * | 2/2000 | Virtanen | 422/68.1 |
| 6,042,709 | A | 3/2000 | Parce et al. | |
| 6,042,710 | A | 3/2000 | Dubrow | |
| 6,046,056 | A | 4/2000 | Parce et al. | |
| 6,062,261 | A | 5/2000 | Jacobson et al. | |
| 6,103,537 | A * | 8/2000 | Ullman et al. | 436/526 |
| 6,150,119 | A * | 11/2000 | Kopf-Sill et al. | 435/7.1 |
| 6,213,151 | B1 | 4/2001 | Jacobson et al. | |
| 6,319,469 | B1 * | 11/2001 | Mian et al. | 422/64 |
| 6,858,185 | B1 * | 2/2005 | Kopf-Sill et al. | 422/100 |
| 6,972,198 | B2 * | 12/2005 | Craig et al. | 436/164 |

FOREIGN PATENT DOCUMENTS

| | | | |
|---|---|---|---|
| WO | WO9604547 | | 2/1996 |
| WO | WO9702357 | | 1/1997 |
| WO | WO 98/00231 | * | 1/1998 |
| WO | WO9800231 | | 1/1998 |
| WO | WO 98/49548 | * | 11/1998 |

OTHER PUBLICATIONS

Shoji et al, Microflow Devices and Systems, 1994, J Micromech Microeng, 4, 157-171.*

Welty et al, Fundamentals of Momentum, Heat, and Mass Transfer, 3rd Ed., 1984, New York: Wiley&Sons, 84-88.*

Dasgupta, P.K. et al., "Electroosmosis: A Reliable Fluid Propulsion System for Flow Injection Analysis," *Anal. Chem.* 66:1792-1798 (1994).

Jacobson, S.C. et al., "Fused Quartz Substrates for Microchip Electrophoresis," *Anal. Chem.* 67:2059-2063 (1995).

Manz, A. et al., "Electroosmotic pumping and electrophoretic separations for miniaturized chemical analysis systems," *J. Micromech. Microeng.* 4:257-265 (1994).

Ramsey, J.M. et al., "Microfabricated chemical measurement systems," *Nature Med.* 1:1093-1096 (1995).

Seiler, K. et al., "Planar Glass Chips for Capillary Electrophoresis: Repetitive Sample Injection, Quantitation, and Separation Efficiency," *Anal. Chem.* 65:1481-1488 (1993).

Seiler, K. et al., "Electroosmotic Pumping and Valveless Control of Fluid Flow Within a Manifold of Capillaries on a Glass Chip," *Anal. Chem.* 66:3485-3491 (1994).

* cited by examiner

*Primary Examiner*—Ann Yen Lam
(74) *Attorney, Agent, or Firm*—Ann C. Peterson; Donald R. McKenna

(57) ABSTRACT

Time dependent iterative reactions are carried out in microscale fluidic channels by configuring the channels such that reagents from different sources are delivered to a central reaction zone at different times during the analysis, allowing for the performance of a variety of time dependent, and/or iterative reactions in simplified microfluidic channels. Exemplary analyses include the determination of dose responses for biological and biochemical systems.

26 Claims, 10 Drawing Sheets

DEVICES, SYSTEMS AND METHODS FOR TIME DOMAIN MULTIPLEXING OF REAGENTS

CROSS-REFERENCE TO RELATED APPLICATION

This application is a division of U.S. patent application Ser. No. 09/238,467, filed Jan. 28, 1999, now abandoned the entirety of which is incorporated herein for all purposes.

BACKGROUND OF THE INVENTION

The biological and chemical sciences, much like the electronics industry, have sought to gain advantages of cost, speed and convenience through miniaturization. The field of microfluidics has gained substantial attention as a potential solution to the problems of miniaturization in these areas, where fluid handling capabilities are often the main barrier to substantial miniaturization.

For example, U.S. Pat. Nos. 5,304,487, 5,498,392, 5,635,358, 5,637,469 and 5,726,026, all describe devices that include mesoscale flow systems for carrying out a large number of different types of chemical, and biochemical reactions and analyses.

Published international patent application No. WO 96/04547 to Ramsey describes microfluidic devices that incorporate electrokinetic means for moving fluids or other materials through interconnected microscale channel networks. Such systems utilize electric fields applied along the length of the various channels, typically via electrodes placed at the termini of the channels, to controllably move materials through the channels by one or both of electroosmosis and electrophoresis. By modulating the electric fields in intersecting channels, one can effectively control the flow of material at intersections. This creates a combination pumping/valving system that requires no moving parts to function. The solid state nature of this material transport system allows for simplicity of fabricating microfluidic devices, as well as simplified and more accurate control of fluid flow.

Published international patent application No. 98/00231 describes the use of microfluidic systems in performing high throughput screening of large libraries of test compounds, e.g., pharmaceutical candidates, diagnostic samples, and the like. By performing these analyses microfluidically, one gains substantial advantages of throughput, reagent consumption, and automatability.

Despite the above-described advances in the field of microfluidics, there still exist a number of areas where this technology could be improved. For example, while electrokinetic material transport systems provide myriad benefits in the microscale movement, mixing and aliquoting of fluids, the application of electric fields can have detrimental effects in some instances. For example, in the case of charged reagents, electric fields can cause electrophoretic biasing of material volumes, e.g., highly charged materials moving at the front or back of a fluid volume. Solutions to these problems have been previously described, see, e.g., U.S. Pat. No. 5,779,868. Alternatively, where one is desirous of transporting cellular material, elevated electric fields can, in some cases result in a perforation or electroporation, of the cells, which may affect there ultimate use in the system.

In addition to these difficulties of electrokinetic systems, microfluidic systems, as a whole, have largely been developed as relatively complex systems, requiring either complex electrical control systems or complex pump and valve systems, for accurately directing material into desired locations. Accordingly, it would be generally desirable to provide microfluidic systems that utilize simplified transport systems, but that are also useful for carrying out important chemical and/or biochemical reactions and other analyses. The present invention meets these and a variety of other needs.

SUMMARY OF THE INVENTION

In a first aspect, the present invention provides a microfluidic device for performing a plurality of successive reactions on at least a first reagent, comprising a body structure. A first reaction zone is disposed within the body structure and is fluidly connected to a source of the at least first reagent. Sources of a second and third reagent are in fluid connection to the first reaction zone. The fluid connections between the second and third reagent sources and the reaction zone are configured to deliver a third reagent from the third reagent source to the first reaction zone subsequent to delivery of a second reagent from the second reagent source to the reaction zone.

The present invention also provides a microfluidic device, comprising a reaction zone and sources of first and second reagents. A first fluid path connects the first reagent source to the reaction zone and is configured to deliver first reagent to the reaction zone under a driving force at a first time point. A second fluid path connects the second reagent source to the reaction zone and is configured to deliver the second reagent to the reaction zone under the driving force at a second time point, the second time point being subsequent to the first time point.

A further aspect of the present invention is a method of performing successive reactions in a microfluidic device. A microfluidic device is provided which comprises a reaction zone disposed within the microfluidic device. The reaction zone is in fluid communication with a source of first reagent, a source of second reagent and a source of third reagent. The fluid connection between the second and third reagent sources and the reaction one is configured to deliver the second reagent to the reaction zone prior to the third reagent. A driving force is applied to at least one of the reaction zone, the first reagent source, the second reagent source and the third reagent source to flow the first reagent through the reaction zone, introduce the second reagent into the reaction zone causing a first reaction between the first reagent and the second reagent, and subsequently introduce the third reagent into the reaction zone to cause a reaction between the first reagent and the third reagent.

DETAILED DESCRIPTION OF THE INVENTION

I. Generally

Figure 1A:
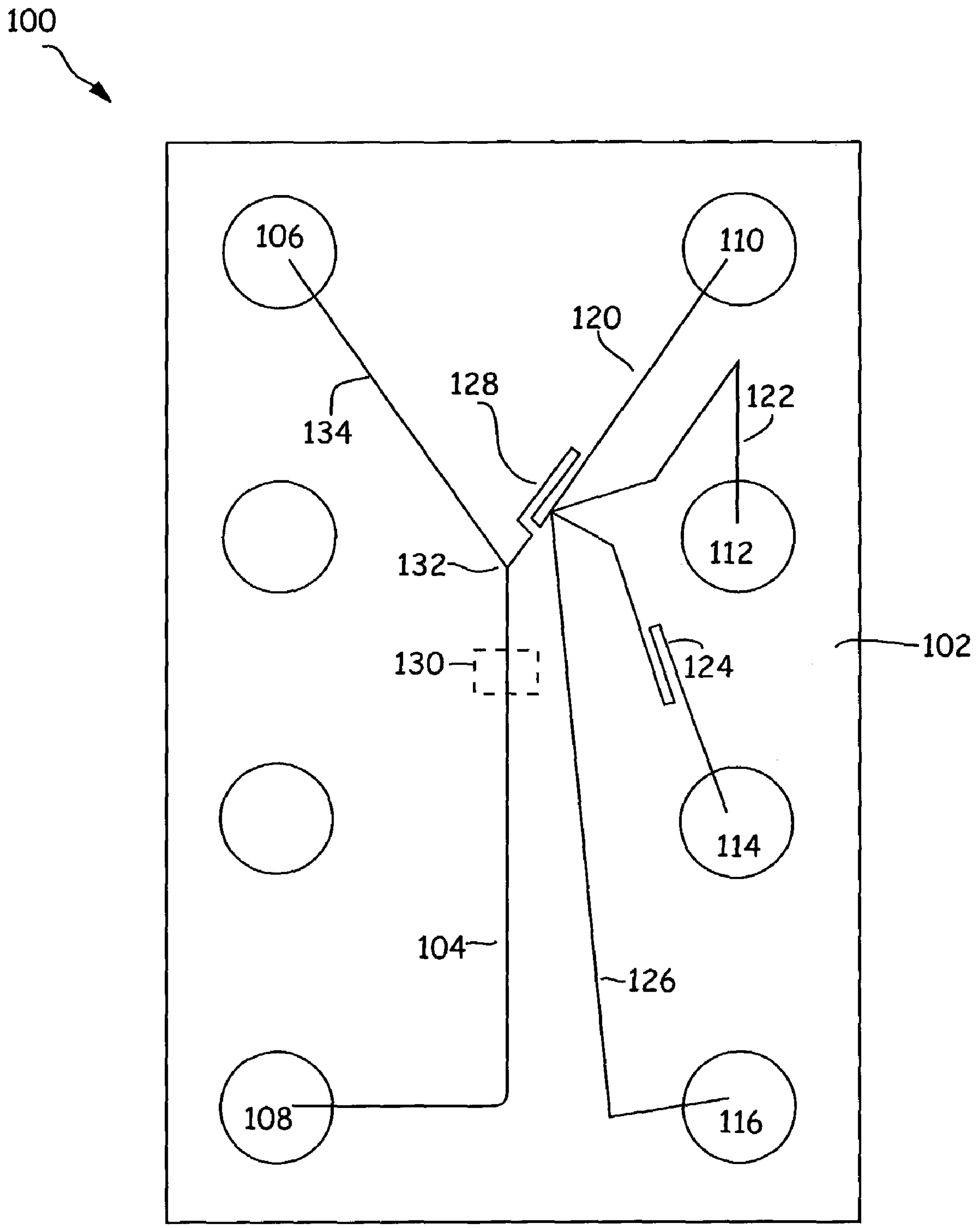
FIGS. 1A and 1B illustrate a microfluidic device for performing serial, iterative reactions within a microscale channel network, according to the present invention.

The present invention generally provides microfluidic devices, systems, kits and methods of using same, for carrying out simplified microfluidic analyses. In brief, the devices and systems of the invention carry out time dependent addition of reagents to a reaction zone from source of those reagents through the structural configuration of the channels that carry those reagents to the reaction zone. This is a drastically different approach from previous systems, which relied upon modulation of forces driving material movement as a method for regulating such time dependent material movement. Restated, instead of turning on pumps and valves at specific times to regulate when and how much of a particular reagent was added to a reaction, the present invention typically relies, at least in part, on the structural characteristics of the channels carrying those reagents to regulate the timing and amount of reagent additions to reactions.

The devices and systems of the present invention offer benefits of greater simplicity over previously described systems which used complex networks of pumps and valves, or electrical controlling systems to selectively move materials through channels in a microfluidic device. By configuring reagent addition channels appropriately, a single driving force can be applied over the whole system, which yields precise time-dependent addition of the reagents to a central reaction channel.

For example, where a plurality of reagent sources are fluidly connected to a reaction zone via appropriate connector channels, one can pull a vacuum on the reaction zone which will draw the reagents into the reaction zone. The amount of time required for a particular reagent to reach the reaction zone via a given channel is dependent upon the driving force applied to the reagent, e.g., the applied vacuum, as well as the structural characteristics of the channel connecting the reagent source with the reaction zone. These structural characteristics include the resistance of the channel to fluid flow, which is typically a function of the cross-sectional area and aspect ratio of the channel, as well as the length of the channel. Accordingly, by adjusting either of these characteristics of the connecting channel, one can adjust the amount of time required for a given reagent to reach the reaction zone from its respective source and/or the rate at which the reagent flows into the reaction zone. Additional reagent sources are then optionally connected to the reaction zone by appropriate connector channels, which connector channels can be configured to introduce reagents into the reaction zone at the same, or predetermined different times from the first reagent.

By "hardwiring" the timing of reagent additions and/or the volumetric rate of reagent additions into the channels of the device, one can employ a single, constant driving force to move the materials through the channels of the device, which allows for much simpler systems for performing a large number of different reactions and/or analyses.

II. Devices

As generally described above, in a first aspect, the present invention provides microfluidic devices for performing a plurality of successive reactions and/or reagent additions to at least one other reagent. As described herein, microfluidic devices of the invention typically comprise a network of microscale or microfabricated channels all disposed within an integrated body structure.

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 μm, and typically between about 0.1 μm and about 500 μm. In the devices of the present invention, the microscale channels or chambers preferably have at least one cross-sectional dimension between about 0.1 μm and 200 μm, more preferably between about 0.1 μm and 100 μm, and often between about 0.1 μm and 50 μm. Accordingly, the microfluidic devices or systems prepared in accordance with the present invention typically include at least one microscale channel, usually at least two intersecting microscale channel segments, and often, three or more intersecting channel segments disposed within a single body structure. Channel intersections may exist in a number of formats, including cross intersections, "T" intersections, or any number of other structures whereby two channels are in fluid communication.

The body structures of the devices which integrate various microfluidic channels, chambers or other elements, as described herein, may be fabricated from a number of individual parts, which when connected form the integrated microfluidic devices described herein. For example, the body structure can be fabricated from a number of separate capillary elements, microscale chambers, and the like, all of which are connected together to define an integrated body structure. Alternatively and in preferred aspects, the integrated body structure is fabricated from two or more substrate layers which are mated together to define a body structure having the channel and chamber networks of the devices within. In particular, a desired channel network is laid out upon a typically planar surface of at least one of the two substrate layers as a series of grooves or indentations in that surface. A second substrate layer is overlaid and bonded to the first substrate layer, covering and sealing the grooves, to define the channels within the interior of the device. In order to provide fluid and/or control access to the channels of the device, a series of ports or reservoirs is typically provided in at least one of the substrate layers, which ports or reservoirs are in fluid communication with the various channels of the device.

A variety of different substrate materials may be used to fabricate the devices of the invention, including silica-based substrates, i.e., glass, quartz, fused silica, silicon and the like, polymeric substrates, i.e., acrylics (e.g., polymethylmethacrylate) polycarbonate, polypropylene, polystyrene, and the like. Examples of preferred polymeric substrates are described in commonly owned published international patent application No. WO 98/46438 which is incorporated herein by reference for all purposes. Silica-based substrates are generally amenable to microfabrication techniques that are well known in the art including, e.g., photolithographic techniques, wet chemical etching, reactive ion etching (RIE) and the like. Fabrication of polymeric substrates is generally carried out using known polymer fabrication methods, e.g., injection molding, embossing, or the like. In particular, master molds or stamps are optionally created from solid substrates, such as glass, silicon, nickel electroforms, and the like, using well known microfabrication techniques.

These techniques include photolithography followed by wet chemical etching, LIGA methods, laser ablation, thin film deposition technologies, chemical vapor deposition, and the like. These masters are then used to injection mold, cast or emboss the channel structures in the planar surface of the first substrate surface. In particularly preferred aspects, the channel or chamber structures are embossed in the planar surface of the first substrate. Methods of fabricating and bonding polymeric substrates are described in commonly owned U.S. Pat. No. 6,123,798, and incorporated herein by reference in its entirety for all purposes.

In preferred aspects, the microfluidic devices of the invention typically include a reaction zone disposed within the overall body structure of the device. The reaction zone is optionally a channel, channel portion or chamber that is disposed within the body structure, and which receives the various reagents, materials, test compounds or the like, which are the subject of the desired analysis. Although preferably used for fluid based reactions and analyses, it will be readily appreciated that the reaction zone can optionally include immobilized reagents disposed therein, e.g., immobilized on the surface of the channel or upon a solid support disposed within that channel. In preferred aspects, the reaction zone is a channel portion that is fluidly connected at a first end to a source of at least a first reagent. The second end of the reaction channel portion is typically fluidly connected to a port disposed in the body structure, which port may function as an access port and/or a waste fluid reservoir, e.g., where reactants may collect following the desired reaction/analysis. The reaction zone typically comprises at least one cross-sectional dimension that is in the range of from about 0.1 μm to about 1 mm, e.g., is of microscale dimensions. Of course, these dimensions will typically vary depending upon the application for which the overall device is to be used. For example, for flowing fluid based reactions/analyses, reaction channel cross-sectional dimensions will typically range between about 1 and about 200 μm, and preferably will fall in the range between about 5 and about 100 μm. For cell bases reactions/analyses, channel dimensions are typically larger to permit passage of the cells, without clogging of the channels. In these cases, reaction channel dimensions are typically in the range of from about 10 μm to about 200 μm, depending upon the cell types that are to be analyzed, e.g., smaller bacterial cells vs. larger mammalian, plant or fungal cells.

As noted above, the first reaction zone is optionally fluidly connected, e.g., at a first end, to a source of a first reagent. In screening applications, e.g., analyses to determine whether a particular material or treatment has an effect on a particular system, the first reagent typically comprises one or more components of a biological or biochemical system against which other reagents are going to be screened. As used herein, the phrase "biochemical system" generally refers to a chemical interaction that involves molecules of the type generally found within living organisms. Such interactions include the full range of catabolic and anabolic reactions which occur in living systems including enzymatic, binding, signaling and other reactions. Further, biochemical systems, as defined herein, will also include model systems which are mimetic of a particular biochemical interaction. Examples of biochemical systems of particular interest for use in the devices and systems described herein include, e.g., receptor-ligand interactions, enzyme-substrate interactions, cellular signaling pathways, transport reactions involving model barrier systems (e.g., cells or membrane fractions), and a variety of other general systems. Cellular or organismal viability or activity may also be screened using the methods and apparatuses of the present invention.

In order to provide methods and devices for screening compounds for effects on biochemical systems, the present invention generally incorporates as the first regent at least a part of a model in vitro system which mimics a given biochemical system in vivo for which effector compounds are desired. The range of systems against which compounds can be screened and for which effector compounds are desired, is extensive. For example, compounds are screened for effects in blocking, slowing or otherwise inhibiting key events associated with biochemical systems whose effect is undesirable. For example, test compounds may be screened for their ability to block systems that are responsible, at least in part, for the onset of disease or for the occurrence of particular symptoms of diseases, including, e.g., hereditary diseases, genetic disorders, cancers, bacterial or viral infections and the like.

Compounds that show promising results in screening assay methods are then typically subjected to further testing to identify effective pharmacological agents for the treatment of disease or symptoms of a disease.

Alternatively, compounds can be screened for their ability to stimulate, enhance or otherwise induce biochemical systems whose function is believed to be desirable, e.g., to remedy existing deficiencies in a patient.

Once a model system is selected, batteries of test compounds can then be applied against these model systems. By identifying those test compounds that have an effect on the particular biochemical system, in vitro, one can identify potential effectors of that system, in vivo.

In their simplest forms, the biochemical system models employed in the methods and apparatuses of the present invention will screen for an effect of a test compound on an interaction between two components of a biochemical system, e.g., receptor-ligand interaction, enzyme-substrate interaction, and the like. In this form, the biochemical system model will typically include the two normally interacting components of the system for which an effector is sought, e.g., the receptor and its ligand, the enzyme and its substrate, or the antibody and its antigen.

Determining whether a test compound has an effect on this interaction then involves contacting the system with the test compound and assaying for the functioning of the system, e.g., receptor-ligand binding or substrate turnover. The assayed function is then compared to a control, e.g., the same reaction in the absence of the test compound or in the presence of a known effector.

Although described in terms of two-component biochemical systems, the methods and apparatuses may also be used to screen for effectors of much more complex systems where the result or end product of the system is known and assayable at some level, e.g., enzymatic pathways, cell signaling pathways and the like. Alternatively, the methods and apparatuses described herein may be used to screen for compounds that interact with a single component of a biochemical system, e.g., compounds that specifically bind to a particular biochemical compound, e.g., a receptor, ligand, enzyme, nucleic acid, structural macromolecule, etc.

Biochemical system models may be entirely fluid-based, or may include solid phase components, i.e., bead bound components, which are flowed through the channels of the devices described herein, or alternatively, are retained within a particular region of the device, e.g., the reaction zone.

Biochemical system models may also be embodied in whole cell systems. For example, where one is seeking to screen test compounds for an effect on a cellular response, whole cells are typically utilized. Cell systems that may be used with the methods, devices and systems of the invention include, e.g., mammalian cells, fungal cells, bacterial cells, yeast cells, insect cells, and the like. Modified cell systems may also be employed in the screening systems encompassed herein, e.g., cells which express non-native receptors, pathways or other elements. For example, chimeric reporter systems may be employed as indicators of an effect of a test compound on a particular biochemical system. Chimeric reporter systems typically incorporate a heterogenous reporter system integrated into a signaling pathway, which signals the binding of a receptor to its ligand. For example, a receptor may be fused to a heterologous protein, e.g., an enzyme whose activity is readily assayable. Activation of the receptor by ligand binding then activates the heterologous protein, which then allows for detection. Thus, the surrogate reporter system produces an event or signal, which is readily detectable, thereby providing an assay for receptor/ligand binding. Examples of such chimeric reporter systems have been previously described in the art.

Alternatively or additionally, cells may be used in conjunction with function specific indicator compounds or labels, e.g., which signal a particular cellular function, such as ion regulation or transport, viability and/or apoptosis, and the like.

Examples of indicators of cellular transport functions, i.e., ion flux, and intracellular pH regulation, are particularly useful in accordance with the cellular systems described herein. In particular, cellular transport channels have been generally shown to be responsive to important cellular events, e.g., receptor mediated cell activation, and the like. For example, G-protein coupled receptors have been shown to directly or indirectly activate or inactivate ion channels in the plasma membrane or endosomal membranes of cells, thereby altering their ion permeability and thus effecting the excitability of the membrane and intracellular ion concentrations. See, Hille, Ionic Channels of Excitable Membranes, Sinauer Assoc. (1984).

In accordance with this aspect of the present invention, therefore, the indicator of cellular function comprises an indicator of the level of a particular intracellular species. In particularly preferred aspects, the intracellular species is an ionic species, such as $Ca^{++}$, $Na^{+}$, $K^{+}$, $Cl^{-}$, or $H^{+}$ (e.g., for pH measurements). A variety of intracellular indicator compounds are commercially available for these ionic species (e.g., from Molecular Probes, Eugene Oreg.). For example, commonly used calcium indicators include analogs of BAPTA (1,2-bis(2-aminophenoxy)ethane-N,N,N',N'-tetraacetic acid), such as Fura-2, Fluo-2 and Indo-1, which produce shifts in the fluorescent excitation or emission maxima upon binding calcium, and Fluo-3 and Calcium Green-2, which produce increases in fluorescence intensity upon binding calcium. See also, U.S. Pat. No. 5,516,911. Sodium and potassium sensitive dyes include SBFI and PBFI, respectively (also commercially available from Molecular Probes). Examples of commercially available chloride sensitive indicators include 6-methoxy-N-(sulfopropyl)quinolinium (SPQ), N-(sulfopropyl) acridinium (SPA), N-(6-methoxyquinolyl)acetic acid, and N-(6-methoxyquinolyl)acetoethyl ester (Molecular Probes, Inc.), all of which are generally quenched in the presence of chloride ions. Similarly, intracellular pH indicators are equally applicable to the systems described herein, including, e.g., SNARFL, SNARF, BCECF, and HPTS indicators, available from Molecular Probes, Inc.

A variety of other detection/labeling mechanisms are also available for detecting binding of one molecule, e.g., a ligand or antibody, to another molecule, e.g., a cell surface receptor. For example, a number of labeling materials change their fluorescent properties upon binding to hydrophobic sites on proteins, e.g., cell surface proteins. Such labels include, e.g., 8-amino-1-naphthalene sulfonate (ANS), 2-p-toluidinylnaphthalene-6-sulfonate (TNS) and the like. Alternatively, detectable enzyme labels are utilized that cause precipitation of fluorescent products on solid phases, i.e., cell surfaces are optionally used as function indicators of binding. For example, alkaline phosphatase substrates that yield fluorescent precipitates are optionally employed in conjunction with alkaline phosphatase conjugates of cell binding components. Such substrates are generally available from Molecular Probes, Inc., and are described in, e.g., U.S. Pat. No. 5,316,906, U.S. Pat. No. 5,443,986.

Viability indicative dyes are generally commercially available. For example, fluorogenic esterase substrates, such as calcein AM, BCECF AM and fluorescein diacetate, can be loaded into adherent or nonadherent cells, and are suitable indicators of cell viability. Specifically, these esterase substrates measure both esterase activity, which is required to activate the fluorescence of the dye, as well as cell-membrane integrity, which retains the fluorescent materials intracellularly. Other suitable viability indicators include polyfluorinated fluorescein derivatives (i.e., DFFDA, TFFDA, HFFDA and $Br_4$TFFDA), polar nucleic acid based dyes (i.e., SYTOX Green™), dimeric and monomeric cyanine dyes (i.e., TOTO™ and TO-PRO™ series dyes from Molecular Probes), ethidium and propidium dyes (i.e., ethidium bromide, ethidium homodimer and propidium iodide).

The use of both function indicators and reference indicators in cell-based assay systems is described in detail in copending commonly owned U.S. patent application Ser. No. 09/104,519, filed Jun. 25, 1998 and incorporated herein by reference.

Additionally, where one is screening for bioavailability, e.g., transport, biological barriers may be included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention will be useful in screening for compounds that have an effect on an interaction between a receptor molecule and its ligands. As used herein, the term "receptor" generally refers to one member of a pair of compounds that specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs may also include antibody/antigen binding pairs, complementary nucleic acids, nucleic acid associating proteins and their nucleic acid ligands. A large number of specifically associating biochemical compounds are well known in the art and can be utilized in practicing the present invention.

A similar, and perhaps overlapping, set of biochemical systems includes the interactions between enzymes and their substrates. The term "enzyme" as used herein, generally refers to a protein which acts as a catalyst to induce a chemical change in other compounds or "substrates."

Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "inducer."

As used herein, the term "test compound" refers to a compound, mixture of compounds, or material that is to be screened for an ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, extracts made from biological materials such as bacteria, plants, fungi, or animal cells or tissues, naturally occurring or synthetic compositions. The largest collections, or "libraries" of test compounds are typically generated using combinatorial chemistry techniques, which produce large numbers of related chemical compounds. In accordance with the present invention, test compounds are typically placed into reservoirs within the device from which they are transported into the main reaction zone. However, in certain aspects, test compounds, biochemical system components, or other components of a given analysis may be external to the device itself, and accessed by an external sampling element, e.g., a pipettor or electropipettor channel, e.g., as described in U.S. Pat. No. 5,779,868.

Accordingly, in preferred aspects, the first reagent source typically comprises one or more components of a biochemical system, e.g., enzyme and substrate combinations, receptor-ligand pairs, complementary nucleic acid sequences, cellular suspensions, or the like. In particularly preferred aspects, the first reagent source has disposed therein a suspension of cells that are to be screened against other reagents or test compounds to identify and/or quantify an effect of those other reagents upon the functions of the cells in that suspension. In optional alternative aspects, the first reagent may comprise a first reagent in a synthesis process that is to be performed within the device, e.g., a chemical precursor.

In order to be able to detect and quantify the results of a particular reaction or other combination of reagents, it is generally desirable that the reaction of interest have a detectable signal associated with it. In particularly preferred aspects, one or more of the interacting components and/or the product of the interaction of those components will produce an optically detectable signal. Examples of such reactions include chromogenic reactions, luminescent reactions, fluorogenic reactions, and the like. These detectable labels and reactions incorporating them are described in substantial detail in Published International Patent Application No. 98/00231, which is incorporated herein by reference in its entirety for all purposes. Additional optically detectable reactions include those whose products and substrates are fluorescent but which fluorescence can be separately quantified whether it is from the substrate or the product, e.g., in mobility shift assays (see, e.g., Published International Application No. WO 98/56956), where the mobility of the product differs from that of the substrate, fluorescence polarization assays, where the binding of a ligand to a receptor significantly alters the spin rate of the complex over the separate components, giving rise to a shift in the level of fluorescence polarization.

In addition to detectable labels associated with the particular reaction that is being analyzed, in some cases, it is desirable to incorporate a background label or labels into the reagent sources to indicate the time and/or concentration at which materials form these sources are introduced into the reaction channel and/or pass the detection point. In particular, by monitoring the relative rate at which different background labels from different reagent sources pass the detection zone, one can back calculate the rate of flow of reagents along the reaction channel from the applied driving force and configuration, e.g., cross-section and length, of the channel segments. Background labels are typically distinguishable from the main reaction signal, e.g., based upon their emission or excitation spectra, if fluorescent, color, if chromophoric, or based upon different detectable principles, e.g., ionic strength or the like. A variety of labeling materials and methods are known in the art.

Additional reagents used in the reaction/analysis, e.g., test compounds, buffers, indicators or the like, are delivered into the reaction zone from their respective reagent sources. These sources are optionally external or integral to the body structure of the device. For example, in some aspects, separate reservoirs of reagents are provided apart from the overall body structure of the device, but with appropriate fluid connections, e.g., tubing, pipettors or other fluid transfer means, to the channels of the device. However, in preferred aspects, the additional reagent sources are integral to the body structure of the device, e.g., incorporated into or otherwise attached to the body structure. For example, such sources are often provided as ports or reservoirs disposed in the body structure and positioned at the end of connecting channels, which provide fluid connection between these reservoirs and the reaction zone.

One or more connecting channels, which intersect the reaction zone are typically provided within the body structure of the device to deliver the various other reagents to the reaction zone, whether the reagent sources are integral to or separate from that body structure. In the case of multiple reagent sources, the connecting channels are optionally provided intersecting with the reaction zone at a single point, either through the convergence of the connecting channels at that point or by the connection of these connecting channels to a common channel which intersects the reaction channel at this point. Alternatively, the connecting channels intersect the reaction zone at two or more separate points on the reaction channel. The precise configuration of the fluid connection between the connecting channel and the reaction zone typically depends upon the particular application for which he microfluidic device is to be used. For example, where one is attempting to individually analyze the effects of multiple different reagents or dilutions of the same reagent successively and cumulatively introduced to the reaction zone, a single intersection point is preferred, e.g., in performing dose response analyses. Alternatively, where one is performing an iterative reaction on the first reagent where one is primarily concerned with the ultimate effect of multiple reagents on the first reagent, which reagents must be separately and iteratively combined, e.g., where one reaction proceeds from the product of a preceding reaction, then separate intersection points are often preferred. In either event, the introduction of the additional reagents to the reaction zone is typically desired to be time dependent. Thus, although generally described for the purposes of performing screening assays and the like, it will be readily appreciated that the devices, systems and methods described herein are useful in performing a number of different types of iterative, time-dependent reactions for a variety of purposes, such as synthetic reaction s, where chemical precursors are flowed through a reaction channel while being iteratively reacted with different reagents at different times to synthesize a desired end product.

As noted above, in accordance with certain aspects of the present invention, either time or volume controlled reagent additions to a particular region of the microfluidic device, e.g., the reaction zone, are carried out by configuring the reagent delivery channels to affect such controlled delivery. In particular, the rate at which material flows through a particular microfluidic channel is defined by a number of factors, including the force applied to drive the material through the channel, the flow resistance of the channel, and the distance that material must travel through the channel. The latter two characteristics are typically dependent upon one or both of the length and cross-sectional dimensions of the channel through which the material is forced. By controlling at least one of these channel characteristics, one can effectively control the time required for the material to move through the channel and/or the volumetric rate at which material flows through that channel. For example, where the connecting channel between a first reagent source and the reaction zone is shorter than the connecting channel between the second reagent source and the reaction zone, under the same pressure level, the first reagent will reach the reaction zone first just by virtue of the longer distance that the second reagent must travel. In addition, the longer channel will have a greater level of flow resistance, further slowing the second reagent relative to the first.

Similarly, where the connecting channels are the same length, but the second channel has a significantly smaller cross-sectional area, again, it will take the second reagent longer to reach the reaction channel than the first reagent. Further, the rate at which the second reagent flows into the reaction channel will also be reduced. Additionally, the differential pressure-based flow of fluids in two channels having different cross-sectional areas is further amplified in those channels having an aspect ratio (width:depth) that is greater than about 5, where one is varying the narrower dimension, e.g., depth, between the two channels. In particular, in these situations, the pressure-based volumetric flow rate of fluids is reduced by the cube of the reduction in channel depth, while the linear velocity of fluid through the channel is reduced by the square of that reduction. For example, in a pressure based system, where the second channel is one tenth as deep as the first channel, the volumetric flow in that second channel will be reduced 1000 fold over the first channel under the same applied pressure. As a result, one can vary he amount of material transported through a channel (volumetric flow) as well as the amount of time required for fluid to traverse a channel (linear velocity) by varying the channel's depth.

Other control methods are optionally used in conjunction with controlling the connecting channel resistance and/or dimensions, e.g., controlling pressure differentials across the overall system or individual connecting channels, applying secondary driving forces to the channels to slow or speed up flow relative to other channels, and the like.

As noted, configuration of channels to deliver reagents to a common reaction zone at different times or at different rates may be accomplished optionally by a number of methods. First, one can simply lengthen or shorten the channel, such that a second reagent requires more time, and encounters greater viscous drag than a first reagent in reaching the reaction zone, and thus reaches the reaction zone later. Alternatively, one can simply vary the cross-sectional area of the channel, e.g., width and/or depth, to alter that channel's resistance, thereby varying one or both of the timing and amount of reagent addition to the reaction zone. Other methods are also available for effectively varying a channel's resistance to flow, including the inclusion of solid or semi-solid matrices within the channel which matrices occupy channel space, thereby increasing flow resistance, the inclusion of pressure resistors at inlet ports to channels, and the like.

An example of an integrated microfluidic device according to the present invention is schematically illustrated in FIG. 1A. As shown, the device 100 includes a body structure 102 in which is disposed a main reaction zone or channel 104 that connects a first reagent source 106 with a port/waste reservoir 108, also disposed in the body structure. A plurality of additional reagent sources 110, 112, 114 and 116 are also disposed within the body structure 102 and fluidly connected to the reaction channel 104 via separate connector channels (120, 122, 124 and 126 respectively). As shown, the various reagent sources comprise reservoirs that are disposed in the body structure 102 of the device 100 and in fluid communication with their respective connector channels.

As is apparent from FIG. 1A, the connector channels 120, 122, 124 and 126 are each configured to deliver the reagents from their respective reservoirs to the reaction zone 104, at different times or at different rates. In the case of the system shown, this is accomplished by providing each of the connecting channels 120, 122, 124 and 126 with increasing channel lengths, and/or decreasing cross-sectional areas respectively. The result of this configuration is that under the same applied driving force, e.g. applying a negative pressure to the reaction channel 104, it will take proportionally longer for the reagent in reagent source 112 to reach the reaction zone than for the reagent in reagent source 110. Similarly, the reagent in reagent source 114 will take longer to reach the reaction zone than the reagent in reagent source 112, with the reagent in reagent source 116 taking the most time to reach the reaction zone 104.

A detector or detection system is typically disposed adjacent to the detection window in order to detect the result of the reactions carried out within the reaction zone. Often, a microfluidic system will employ multiple different detection systems for monitoring the output of the system, e.g., detecting multiple characteristics of a single reaction zone or detecting the same or different characteristics from a plurality of reaction zones operating in parallel. Examples of detection systems include optical sensors, temperature sensors, pressure sensors, pH sensors, conductivity sensors, and the like. Each of these types of sensors can be readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source, which produces light at an appropriate wavelength or wavelengths for activating the fluorescent material, as well as optics for directing the light source through the detection window to the material contained in the channel or chamber. The light source may be any number of light sources that provides the appropriate wavelength, including lasers, laser diodes and LEDs. In certain aspects, multi-wavelength detection schemes are employed, which employ detectable labels that either excite or emit at different wavelengths, thus allowing their separate detection within a single detection zone, simultaneously. As a result, one or more light sources are typically employed, which produce the necessary wavelengths for exciting these detectable labels. Other light sources may be required for other detection systems. For example, broad band light sources are typically used in light scattering/transmissivity detection schemes, and the like. Typically, light selection parameters are well known to those of skill in the art.

Figure 5:
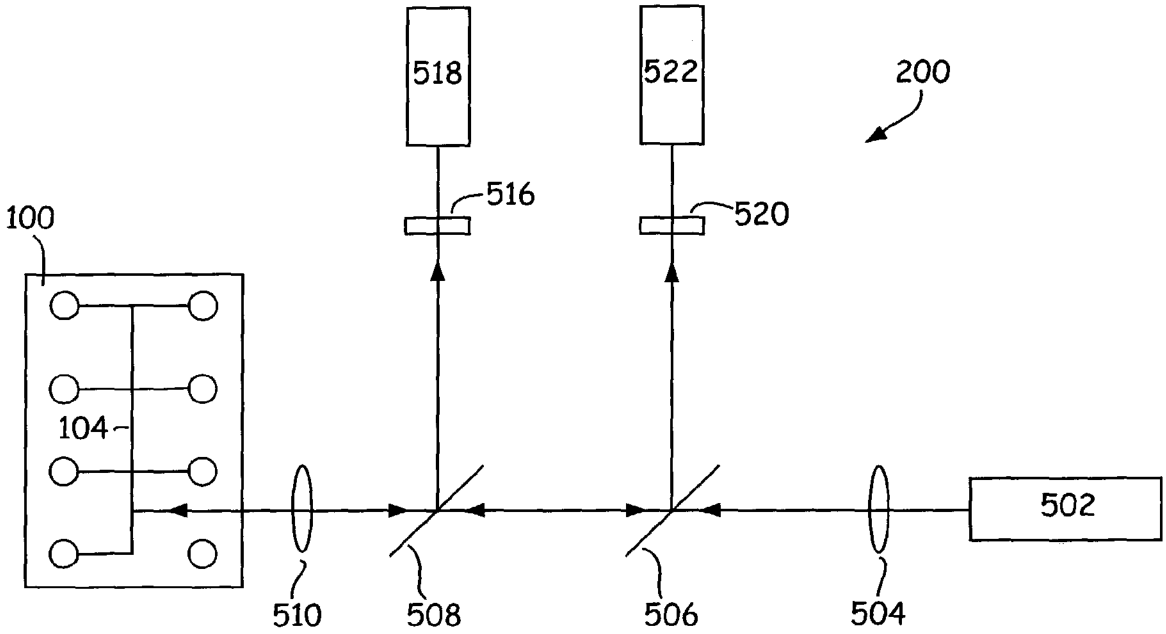
FIG. 5 is a schematic illustration of a multi-wavelength fluorescent detection system
Figure 6:
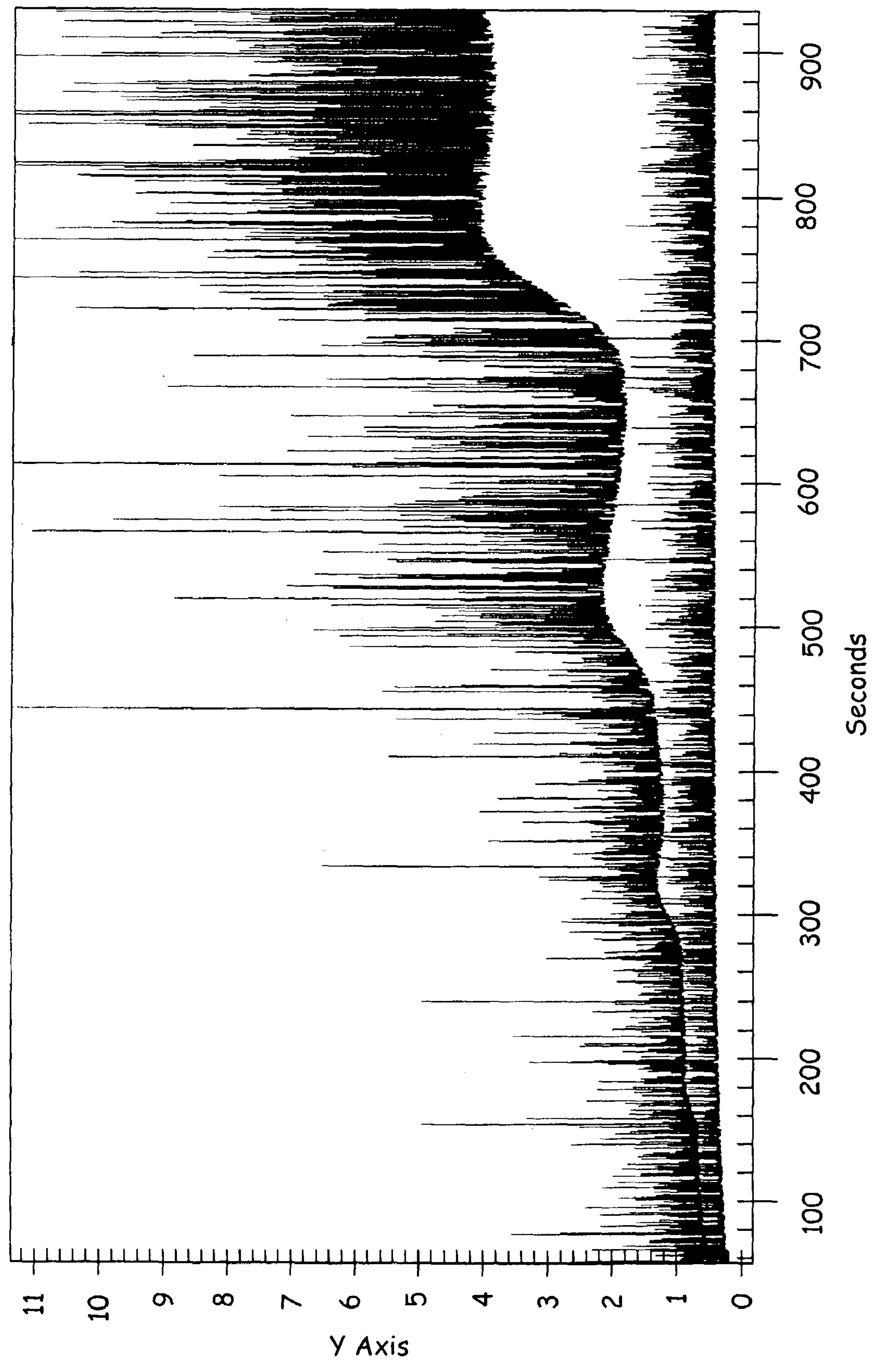
FIG. 6 is a plot of fluorescence versus time of a model cellular system for assaying calcium flux using a fluorescent intracellular calcium indicator.

An example of a multiwavelength detection system is illustrated in FIG. 5. As shown, detector 200 optionally includes one or more different detectors, and is selected to detect both the reference and function labels present in the cells. For example, in the case of cells that include reference and function labels that are fluorescent, the detector typically includes a dual wavelength fluorescent detector. A schematic illustration of such a detector is shown in FIG. 6. As shown, the detector 200 includes a light source 502. Appropriate light sources may vary depending upon the type of detection being employed. For example, in some cases broad spectrum illumination is desirable while in other cases, a more narrow spectrum illumination is desired. Typically, the light source is a coherent light source, such as a laser, or laser diode, although other light sources, such as LEDs, lamps or other available light sources are also optionally employed. In the case of a fluorescent detector, excitation light, e.g., light of appropriate wavelength to excite both reference and function labels, from the light source 502 is directed at the analysis channel 104, e.g., disposed in microfluidic device 100, via an optical train that includes optional lens 504, beam splitters 506 and 508 and objective lens 510. Upon excitation of both the reference and function labels present in channel 514, e.g., associated with cells in the channel, the emitted fluorescence is gathered through the objective lens 510 and passed through beam splitter 508. A portion of the emitted fluorescence is passed through a narrow band pass filter 516 which passes light having a wavelength approximately equal to the excitation maximum (the emitted fluorescence) of one of the two labels, while filtering out the other label's fluorescence, as well as any background excitation light. Another portion of the emitted fluorescence is passed onto beam splitter 506 which directs the fluorescence through narrow band pass filter 520, which passes light having the wavelength approximately equal to the emission maximum of the other label group. One or more of beam splitters 508 and 506 are optionally substituted with dichroic mirrors for separating the label fluorescence and/or any reflected excitation light. Detectors 518 and 522 are typically operably coupled to a computer which records the level of detected light as a function of time from the beginning of the assay.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Figure 2:
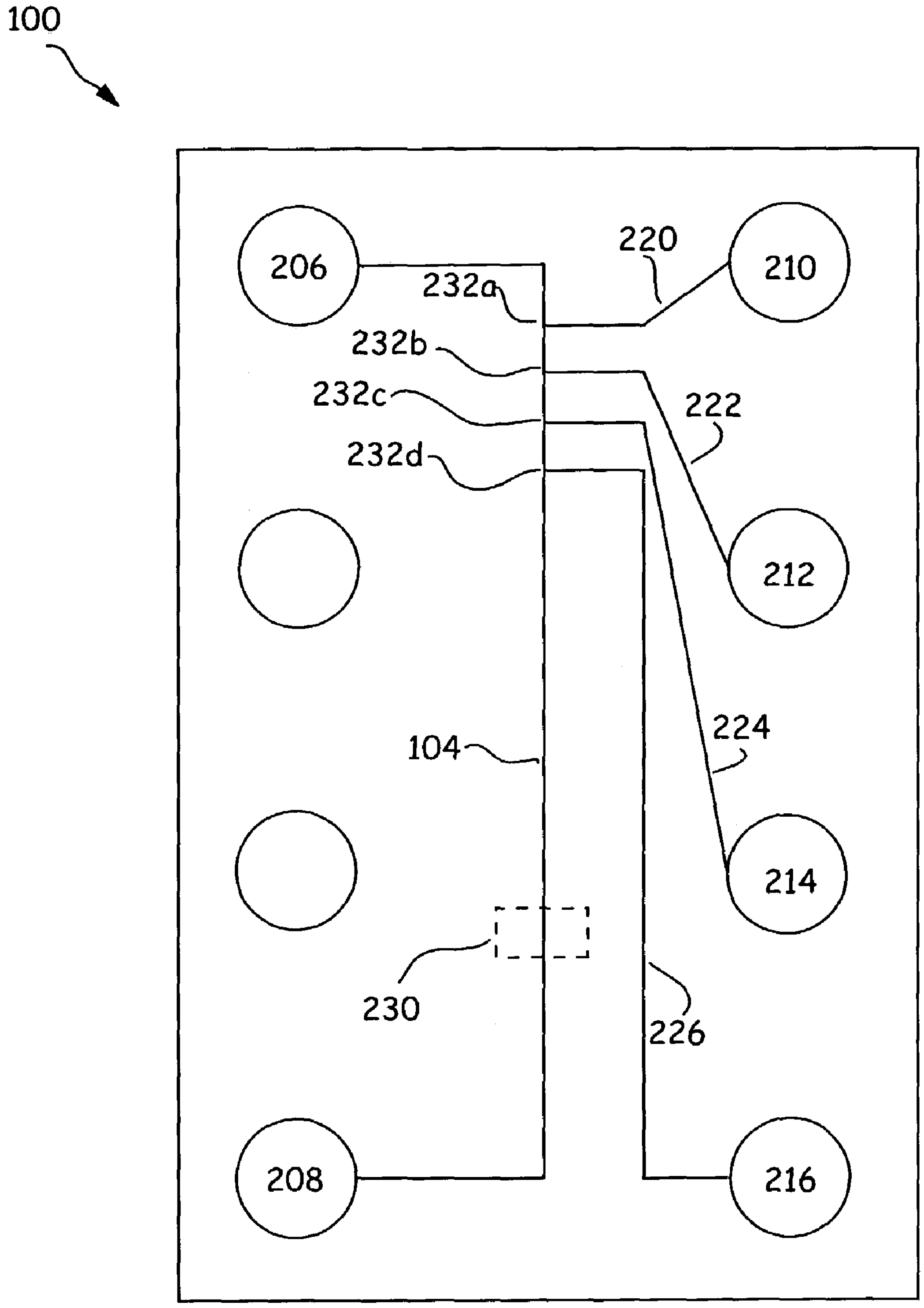
FIG. 2 illustrates an alternate device geometry for performing a plurality of iterative reactions within a microscale channel network.

An alternate channel configuration for the devices of the invention is illustrated in FIG. 2. The device shown is particularly suited for performing successive reactions on a particular first reagent, e.g., where the action of one reagent is dependent upon the action of a previously introduced reagent. Examples of such reactions include, e.g., methods of sequencing nucleic acids by incorporation, e.g., as described in U.S. Pat. Nos. 4,863,849 to Malemede, 4,971,903 to Hyman, and the like.

As shown, the device 100 again includes a main reaction zone 104 that connects a first reagent source 206 to a waste reservoir/port 208. A plurality of additional reagent sources 210-216 are again provided within the integrated body structure of the device 100. These reagent sources are connected to the reaction channel via connecting channels 220-226, respectively. Unlike the device shown in FIG. 1A, however, the connecting channels of the device of FIG. 2 each intersect the reaction zone 104 at a different point along that reaction zone or channel, e.g., intersections 232*a*, 232*b*, 232*c* and 232*d*, respectively. A detection window 230 is also typically provided through which detectable signals from the assay of interest may be monitored.

The devices of the present invention are optionally included as a portion of a kit for performing a desired analysis. Typically, such kits include one or more microfluidic devices as described herein, as well as appropriate volumes of the first, second, third, fourth and other reagents that are to be used in that analyses. These reagents are typically appropriately formulated for the analysis to be performed. The kits also typically include appropriate instructions for their use. The various components of the kits are then typically packaged in a single packaging unit for ease of use and supply.

The devices of the present invention are typically utilized in conjunction with instrumentation to control the operation of and receive data from the microfluidic devices. As such, the instrumentation typically includes a detector or detection system as substantially described above. The instrumentation also typically includes a material transport system, which drives and controls the movement of material through the channels of the device. For example, in certain aspects, the instrumentation optionally includes pressure or vacuum sources, which are used to move fluids or other materials through the channels of the device. Alternative pressure-based systems include, e.g., the use of a wicking material placed into contact with a waste well. The wicking of material from the waste well permits capillary forces in the waste well to uniformly draw material into the waste well from the channel network, and/or eliminates any hydrostatic back-pressure from building up in the waste well.

In the case of applied vacuum or pressure, the instrumentation also typically includes a vacuum or pressure port that is configured to interface with a complementary port on the microfluidic device, e.g., a vacuum port at waste reservoir/port 108/208 of FIGS. 1 and 2. Alternatively, or additionally, the instrumentation includes electrical control systems that are used to impart electrokinetic forces to the materials within the channels of the microfluidic devices, e.g., via electrodes placed in contact with fluids in the reagent sources and waste reservoirs. The use of electrokinetic material transport systems has been described in detail in, e.g., U.S. Pat. No. 5,842,787, which is incorporated herein by reference in its entirety for all purposes. In the case of systems described herein, electrokinetic forces are applied to impart material movement similar to that imparted by pressure-based systems. For example, by applying a single voltage at all of the different reagent wells, and a single current at the waste well/port, one can create potential gradients across the channels of the system to impart fluid flow (See, e.g., U.S. Pat. No. 5,800,690, incorporated herein by reference). Further, by configuring the reagent channel dimensions appropriately, one can dictate the timing and/or amount of reagent addition to the reaction zone, without having to vary the applied electrical fields.

Figure 3:
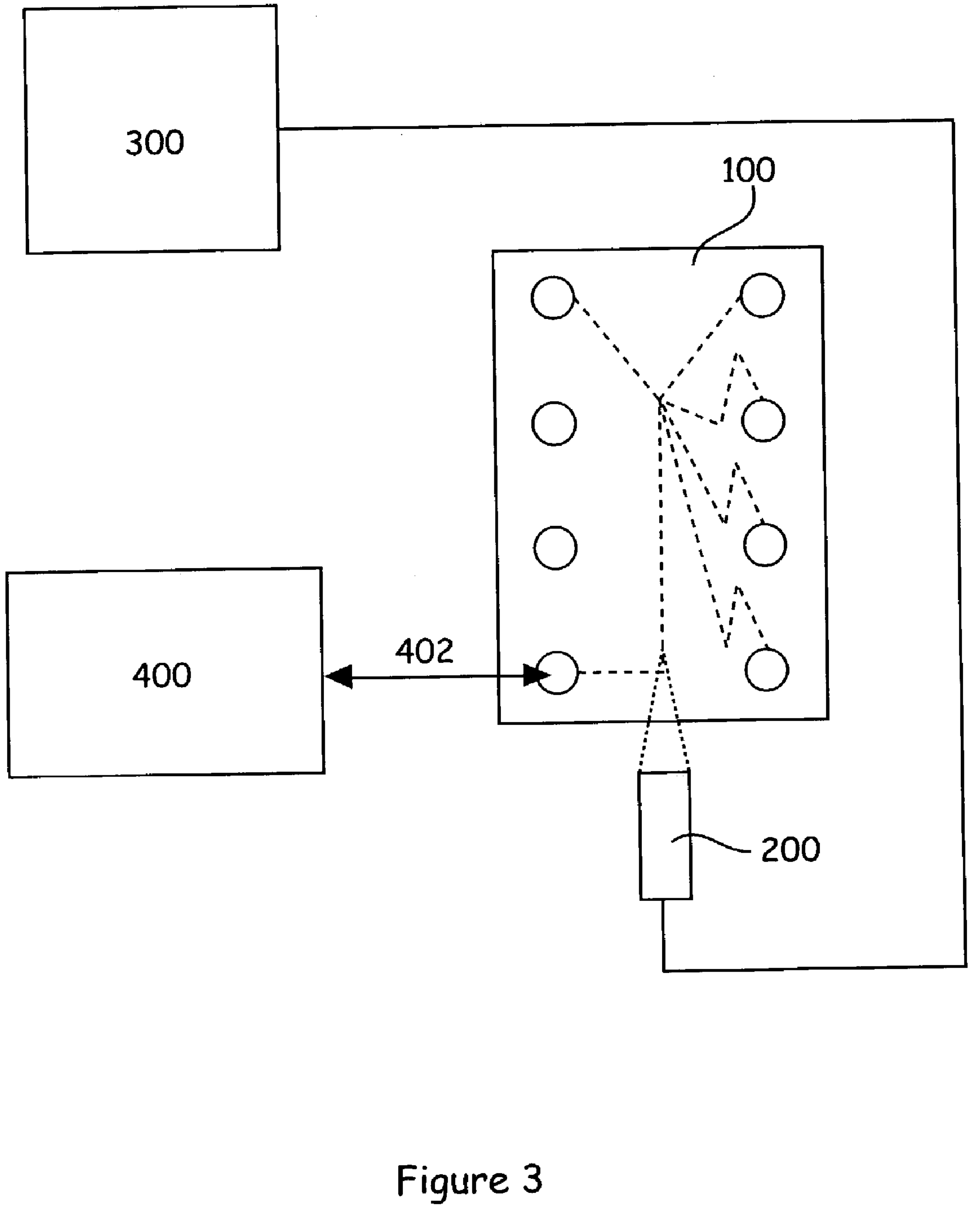
FIG. 3 is a schematic illustration of a complete system for performing iterative reactions within a microfluidic device.

An example of an overall system including the microfluidic devices of the present invention as well as appropriate ancillary equipment is illustrated in FIG. 3. As shown, the overall system includes a microfluidic device 100, a detection system 200 disposed in sensory communication with the reaction channel of the device 100, a computer 300 operably coupled to the detector 200, and an optional material transport system 400 that is operably coupled to at least one channel and/or reservoir of the device 100, for affecting the movement of fluids or other materials through the device. As noted above, material transport system 400 is optionally a vacuum/pressure source that applies a pressure differential across the channels of the device to force/draw materials through those channels. This is typically accomplished by coupling the vacuum or pressure source to at least one reservoir of the device, e.g., waste well 108 as shown, via an appropriate vacuum or pressure coupling between the vacuum or pressure source and the at least one reservoir/port, shown as connection 402. For example vacuum/pressure line having a fitted coupler at one end, e.g., having an appropriate gasket or o-ring, is placed into or over the desired reservoir to provide a sealed pressure connection between the reservoir and the vacuum or pressure source.

Alternatively, material transport system 400 comprises an electrokinetic material transport system, as described above, which is operably coupled to the at least two reservoirs, and preferably a plurality of the reservoirs of the device 100, via appropriate electrical leads/electrodes that are placed into contact with fluids disposed within the reservoirs. In such cases, the material transport system typically comprises at least one, and preferably, two or more power supplies that are separately controllable or are responsive to one another, e.g., as described in commonly owned U.S. Pat. No. 5,800,690.

Figure 4A:
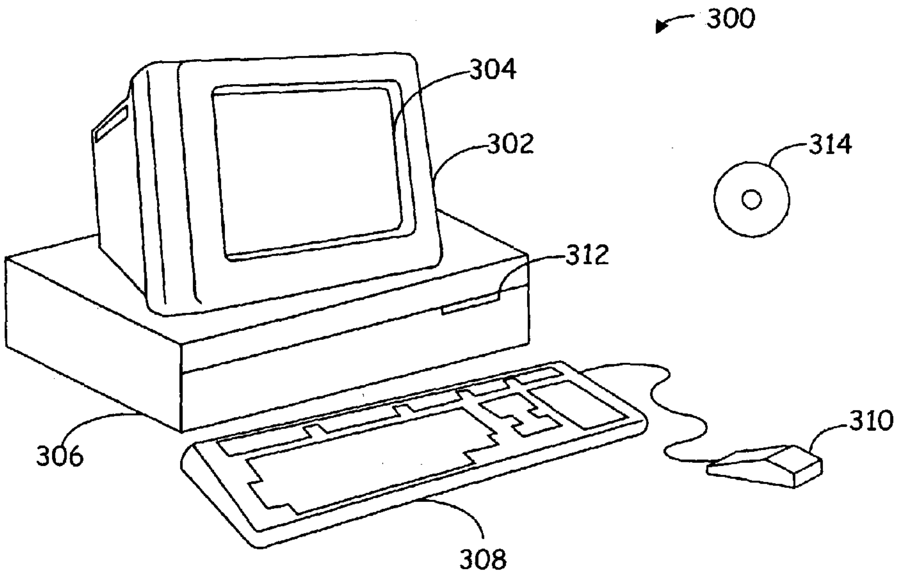
FIGS. 4A and 4B illustrate an exemplary computer system and architecture, respectively, for use in conjunction with the devices, systems and methods of the present invention.
Figure 4B:
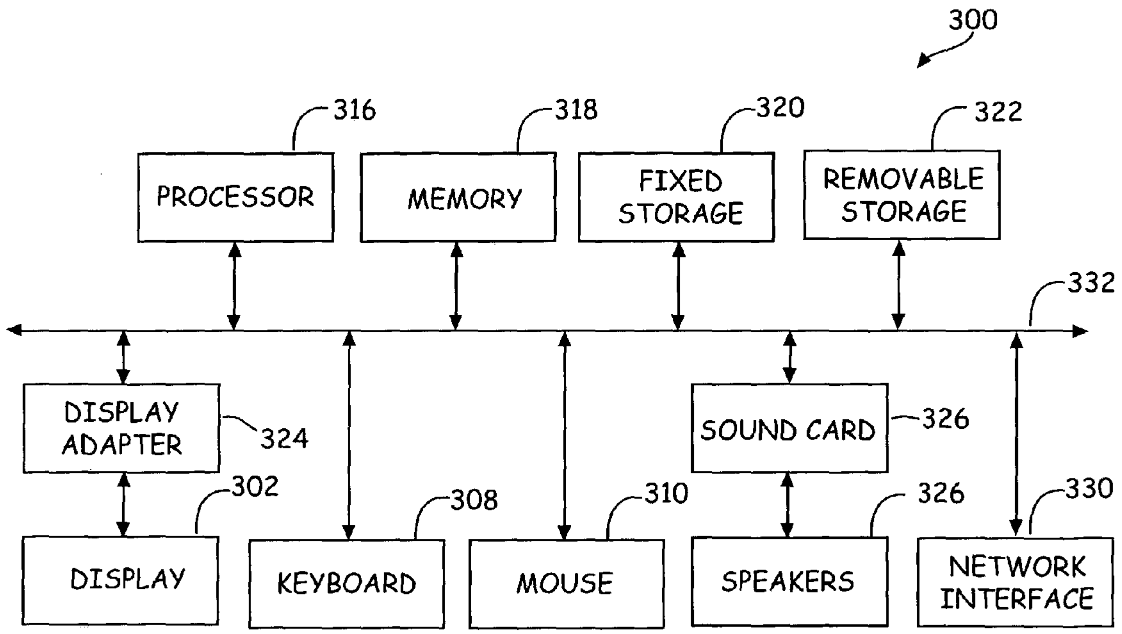

Computer 300 is illustrated in greater detail in FIGS. 4A and 4B. In particular, FIG. 4A illustrates an example of a computer system that may be used to execute software for use in practicing the methods of the invention or in conjunction with the devices and/or systems of the invention. Computer system 300 typically includes a display 302, screen 304, cabinet 306, keyboard 308, and mouse 310. Mouse 310 may have one or more buttons for interacting with a graphical user interface (GUI). Cabinet 306 typically houses a CD-ROM drive 312, system memory and a hard drive (see FIG. 4B) which may be utilized to store and retrieve software programs incorporating computer code that implements the methods of the invention and/or controls the operation of the devices and systems of the invention, data for use with the invention, and the like. Although CD-ROM 314 is shown as an exemplary computer readable storage medium, other computer readable storage media, including floppy disk, tape, flash memory, system memory, and hard drive(s) may be used. Additionally, a data signal embodied in a carrier wave (e.g., in a network, e.g., internet, intranet, and the like) may be the computer readable storage medium.

FIG. 4B schematically illustrates a block diagram of the computer system 300, described above. As in FIG. 4A, computer system 300 includes monitor or display 302, keyboard 308, and mouse 310. Computer system 300 also typically includes subsystems such as a central processor 316, system memory 318, fixed storage 320 (e.g., hard drive) removable storage 322 (e.g., CD-ROM drive) display adapter 324, sound card 326, speakers 328 and network interface 330. Other computer systems available for use with the invention may include fewer or additional subsystems. For example, another computer system optionally includes more than one processor 314.

The system bus architecture of computer system 300 is illustrated by arrows 332. However, these arrows are illustrative of any interconnection scheme serving to link the subsystems. For example, a local bus could be utilized to connect the central processor to the system memory and display adapter. Computer system 300 shown in FIG. 4A is but an example of a computer system suitable for use with the invention. Other computer architectures having different configurations of subsystems may also be utilized, including embedded systems, such as on-board processors on the controller detector instrumentation, and "internet appliance" architectures, where the system is connected to the main processor via an internet hook-up.

The computer system typically includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the optional material transport system, and/or for controlling, manipulating, storing etc., the data received from the detection system. In particular, the computer typically receives the data from the detector, interprets the data, and either provides it in one or more user understood or convenient formats, e.g., plots of raw data, calculated dose response curves, enzyme kinetics constants, and the like, or uses the data to initiate further controller instructions in accordance with the programming, e.g., controlling flow rates, applied temperatures, reagent concentrations, etc.

III. Methods

In addition to the microfluidic devices and systems described above, the present invention also provides methods of using the devices and systems in performing iterative or successive reactions on a first reagent material. Typically, these methods utilize the microfluidic devices as described above, which comprises a reaction zone disposed within the microfluidic device. The reaction zone is in fluid communication with a source of first reagent, a source of second reagent and a source of third reagent. The fluid connection between the second and third reagent sources and the reaction one is typically configured to deliver the second reagent to the reaction zone prior to the third reagent.

As noted above, a driving force is applied to at least one of the reaction zone, the first reagent source, the second reagent source and the third reagent source. The application of the driving force causes the first reagent to move through the reaction zone, and introduce the second reagent into the reaction zone, thereby causing a first reaction between the first reagent and the second reagent. The driving force subsequently causes the introduction of the third reagent into the reaction zone to cause a reaction between one of the first reagent, the second reagent or a product thereof, and the third reagent.

Typically the driving force is selected from any of those described above, including pressure and/or vacuum, electrokinetic forces, centripetal forces, e.g., when the device is configured in a rotor orientation. However, in particularly preferred aspects, the driving force comprises at least in part, the application of a vacuum at the waste reservoir/port of the device. Application of the vacuum draws the first, second and third reagents toward, into and through the reaction zone. Because the channels connecting the reagent sources and the reaction zone are appropriately configured, the reagents will be introduced into the reaction zone in an appropriate order.

The devices of the invention are particularly useful in generating dose response curves for a particular effector of a biochemical system. In brief, and with reference to FIG. 1A, above the overall system is generally filled with an appropriate buffer system, e.g., by placing the buffer into waste reservoir 108 and allowing it to wick through the channels out to the various reagent sources/reservoirs. The components of a biochemical system, e.g., a cellular suspension, are placed into reagent source 106. A first, relatively low concentration of the effector material or test compound is placed into reagent source 110. The next higher concentration of the effector material is placed into reagent source 112, a higher still concentration of the material is placed into reagent source 114, and the highest relative concentration of the effector material is placed into reagent source 116. Application of a single driving force on each of the channels then causes the material in each of the reagent sources to move toward the reaction zone substantially at the same volumetric rate. Examples of such single driving forces optionally include, e.g., a negative pressure applied through the reaction zone 104, e.g., applied via at least waste reservoir 108, or alternatively, a constant and equivalent positive pressure applied to each of the reagent sources 106-116.

In some cases, the negative pressure applied to the reaction zone 104 is applied via both waste reservoir 108 and reagent source 106. Specifically, where flow resistance is not substantial between these reservoirs, e.g., is substantially less than that in the connecting channels 120-126, application of a single negative pressure to waste reservoir 108 would only draw the reagents from source 106. However, by applying a first vacuum to the waste reservoir 108, and a second, lesser vacuum to the reagent source 106, one can modulate the flow of the reagent from source 106 to reservoir 108, while still applying an optimal pressure differential between the reaction zone 104 and the reagent sources 110-116, which are all maintained, e.g., at ambient pressure. This is but one example of the pressure/vacuum modulations that may be accomplished in accordance with the methods and systems of the present invention.

Although described for purposes of exemplification as a single driving force, it will be appreciated that combinations of driving forces may be used to provide even greater variability and controllability to the movement of materials within the devices described herein. For example, a single vacuum may be applied at the waste reservoir/port, while differing positive pressures, or differing pressure resistances may be applied at the reagent sources, to vary the flow rates of materials flowing from those reagent sources. Pressure resistance at the separate reagent sources is optionally supplied through the use of barriers provided over the sources, which barriers have different levels of permeability, for the different sources. Examples of such barriers include porous plugs, filter membranes, and the like.

Figure 1B:
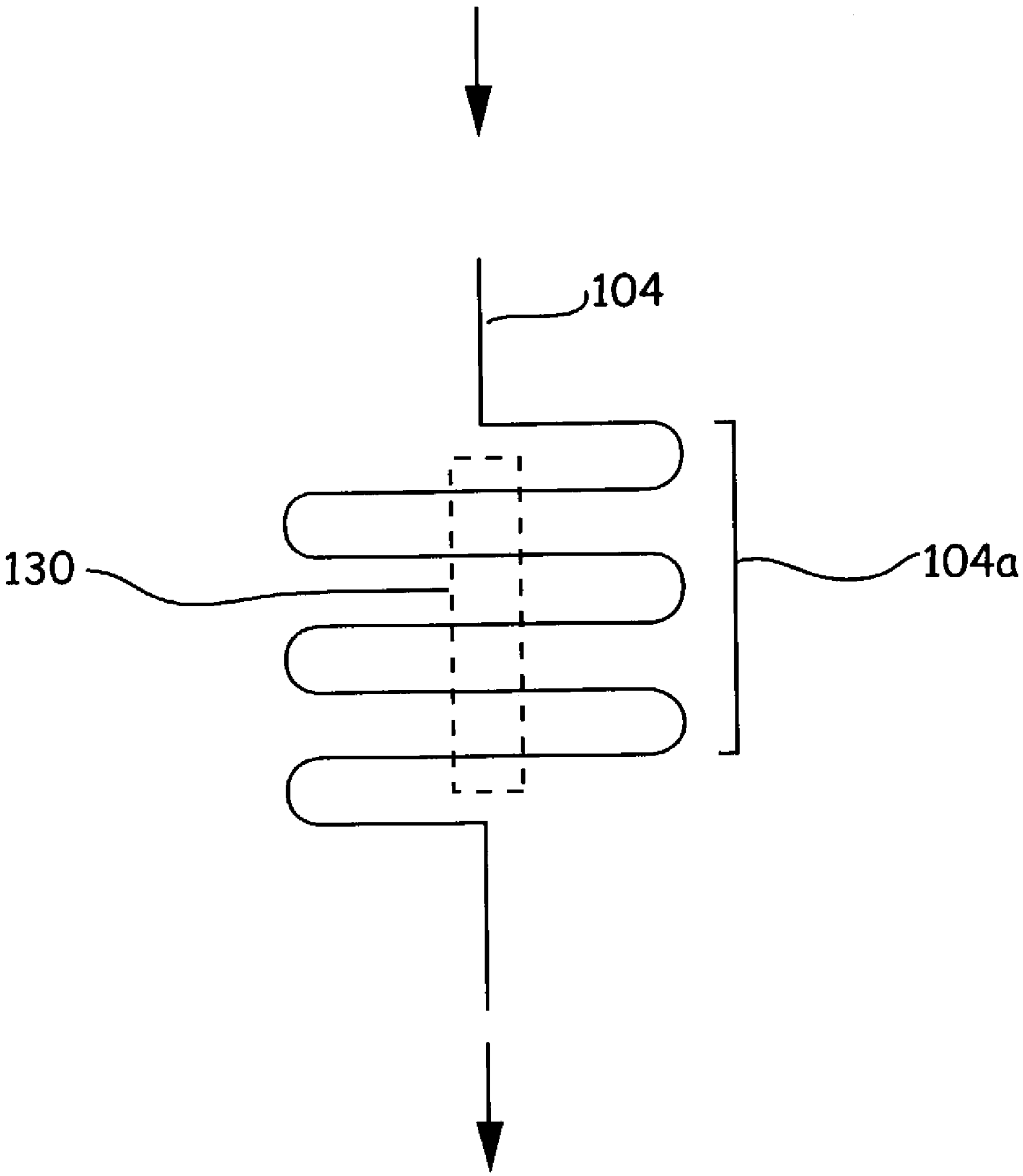

Because the connecting channels 120-126 are of different lengths, the reagent from each source will reach the reaction zone at a different time under the same applied driving force. As such, the lowest concentration of the effector material, e.g., from source 110, reaches the reaction zone first, and the biochemical system components exposed to that concentration of effector material move through the reaction zone and past the detection window 130, where the results of the particular concentration of effector material are detected and quantified. As will be appreciated, reaction or incubation time for a given assay prior to detection is at least partially dictated by the position of detection point 130 along the reaction channel 104. Specifically, the further detection window 130 is from intersection 132, the longer the biochemical system components are exposed to the test compounds prior to detection. Thus, one can obtain different incubation times by varying the location of the detection point 130. Similarly, one can obtain multiple data points relating to different incubation times by including multiple detection points along reaction channel 104, e.g., providing a time-course for the reaction. A variety of channel configurations may also be employed to facilitate such multiple detection points, including, for example, serpentine channels, coiled channels, and even straight channels. FIG. 1B illustrates the use of a serpentine portion **104*a* of reaction channel 104. By using the serpentine channel portion 104*a*, a single scanning detection system may be used to scan the entire detection window 130, covering adjacent portions or loops of the serpentine channel. Although shown as including equal sized loops or "switchbacks", serpentine channel portion 104*a*** optionally includes loops of increasing length in the direction of flow, and preferably of logarithmically increasing lengths. This permits obtaining greater sampling numbers at early time points when biochemical system responses to stimuli more rapid, and fewer sampling numbers at later time points, where these responses have slowed.

A variety of scanning detection systems for detecting from multiple points in a reaction channel have been previously described, e.g., galvo scanners or oscillating laser induced fluorescent detectors, array detectors, e.g., CCD cameras, and the like. In the case of the serpentine channel segment **104*a* shown in FIG. 1B, each scanned portion or loop of the serpentine channel, e.g., those segments within detection window 130, represents a different time point in exposure of the biochemical system components to the test compound. Data obtained from each of these points in the reaction channel 104/104*a*** thus represents the assayed activity at different points following an assayed event, e.g., introduction of a test compound.

Because of the longer connector channel, the next higher concentration of effector material, e.g., from source 112, reaches the reaction zone short period later and interacts with the biochemical system components. Of course this subsequent reaction mixture also includes the more dilute reagent from reagent source 110, which continues to flow into the reaction zone from reagent source 110. However, the level of dilution from this prior reagent addition is easily calculated and taken into account when ultimately analyzing the dose response curve. The effect of the higher concentration of the effector material is then detected and quantified at the detection window. This is repeated when the reagent concentration from reagent source 114 reaches the reaction zone 104, until finally, the highest concentration of the effector material, e.g., from source 116, reaches the reaction channel and interacts with the biochemical system components, flows along the reaction zone, and past the detection window where it is detected and quantified. The single intersection point of the four reagent channels with the reaction zone, e.g., intersection 132, allows the first reagent to be exposed to the different concentrations of the effector material for the same period of time prior to the detection of the effect of that material on the first reagent.

By then plotting out the effect of the increasing concentration of effector material on the components of the biochemical system, one can generate a dose response curve for that effector material. An example of the use of these systems in preparing dose response curves is described in greater detail in Example 1, below.

IV. EXAMPLES

The device shown in FIG. 1A was used to test the dose response of a human monocytic leukemia cell line that carried the Gq coupled P2u purinergic receptor (THP-1), as a model calcium flux assay. Briefly, a phospholipase C/IP3/calcium signal transduction pathway is activated when the receptor binds to its ligand UTP. When the cells are preloaded with a calcium sensitive indicator, i.e., Fluo-3 or Fluo-4 (available from Molecular Probes, Eugene, Oreg.). The transient increase in intracellular calcium is then detected as a fluorescent signal.

In the present example, THP-1 cells were preloaded with Fluo-3 or Fluo-4, as well as a nucleic acid stain (Syto-62 from Molecular Probes). The cells were washed and resuspended in Cell Buffer (1.56 ml HBSS, 0.94 ml 33% Ficoll, 5 μl HEPES (1 M stock), 25 μl 100× PBC, 25 μl 10% BSA, and 0.546 ml OPTI-Prep (65% stock)) and added to reservoir 106. Different concentrations of UTP in Cell Buffer (100, 300, 1000 and 3000 nM, respectively) were then added to reagent reservoirs 110-116. Flow of cells and reagents was initiated by placing a wicking material into the waste well, specifically, two wetted glass fiber filter discs, cut to the dimensions of the waste well and stacked into well 108. A fluorescent detector employing a blue LED as an excitation source was focused at a point 130 in the reaction channel 104, 3 mm from the intersection 132 of the reaction channel 104 and the various connecting channels 120-126 and 134 ("the cell-drug intersection"). The system had a flow rate of 0.2 mm sec., which resulted in detection of cellular response 15 seconds after initial exposure to the UTP solutions. The configuration of the connecting channels 120-126 with differing lengths sequentially exposed the cells to increasing concentrations of UTP, e.g., 100 nM, 300 nM, 1000 nM and 3000 nM.

Figure 7:
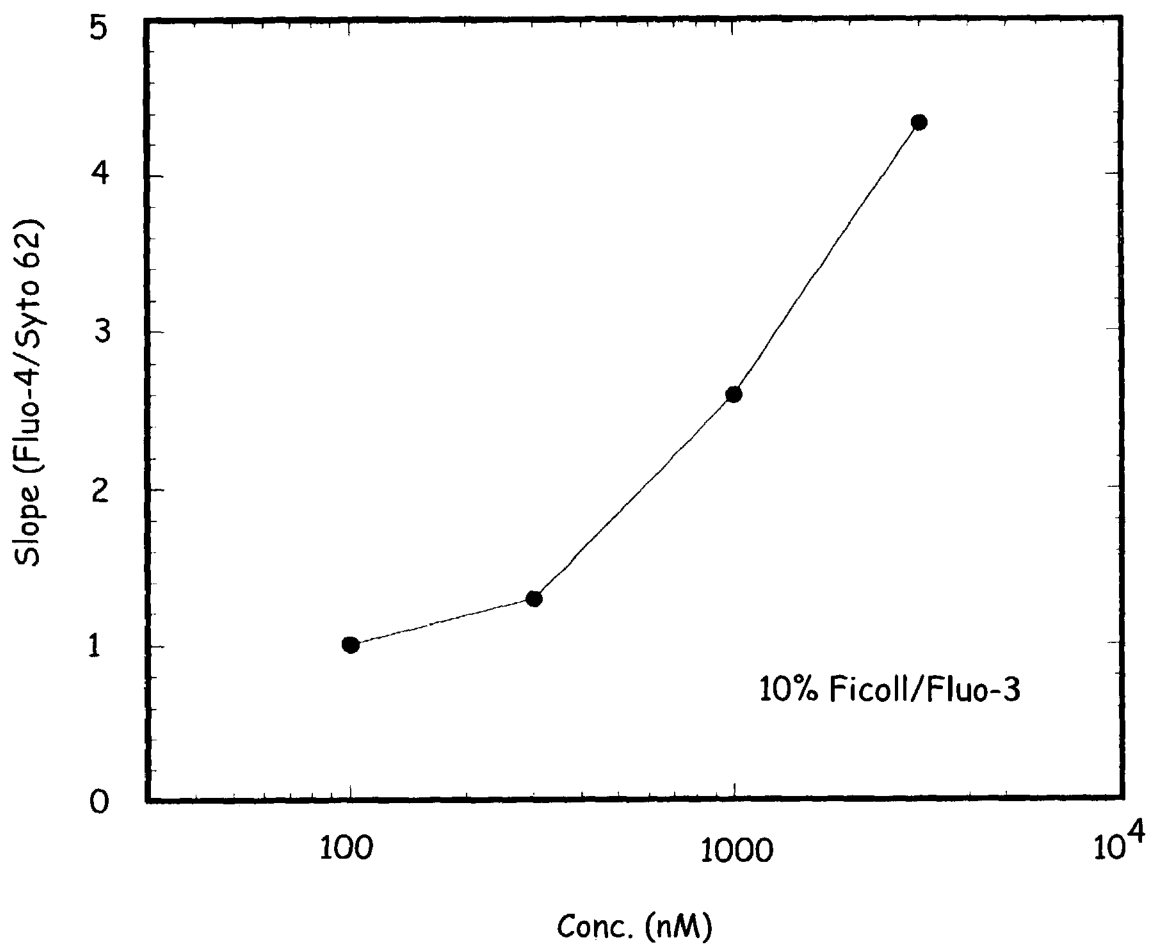
FIG. 7 illustrates a dose response curve generated from the data shown in FIG. 6.
Figure 8:
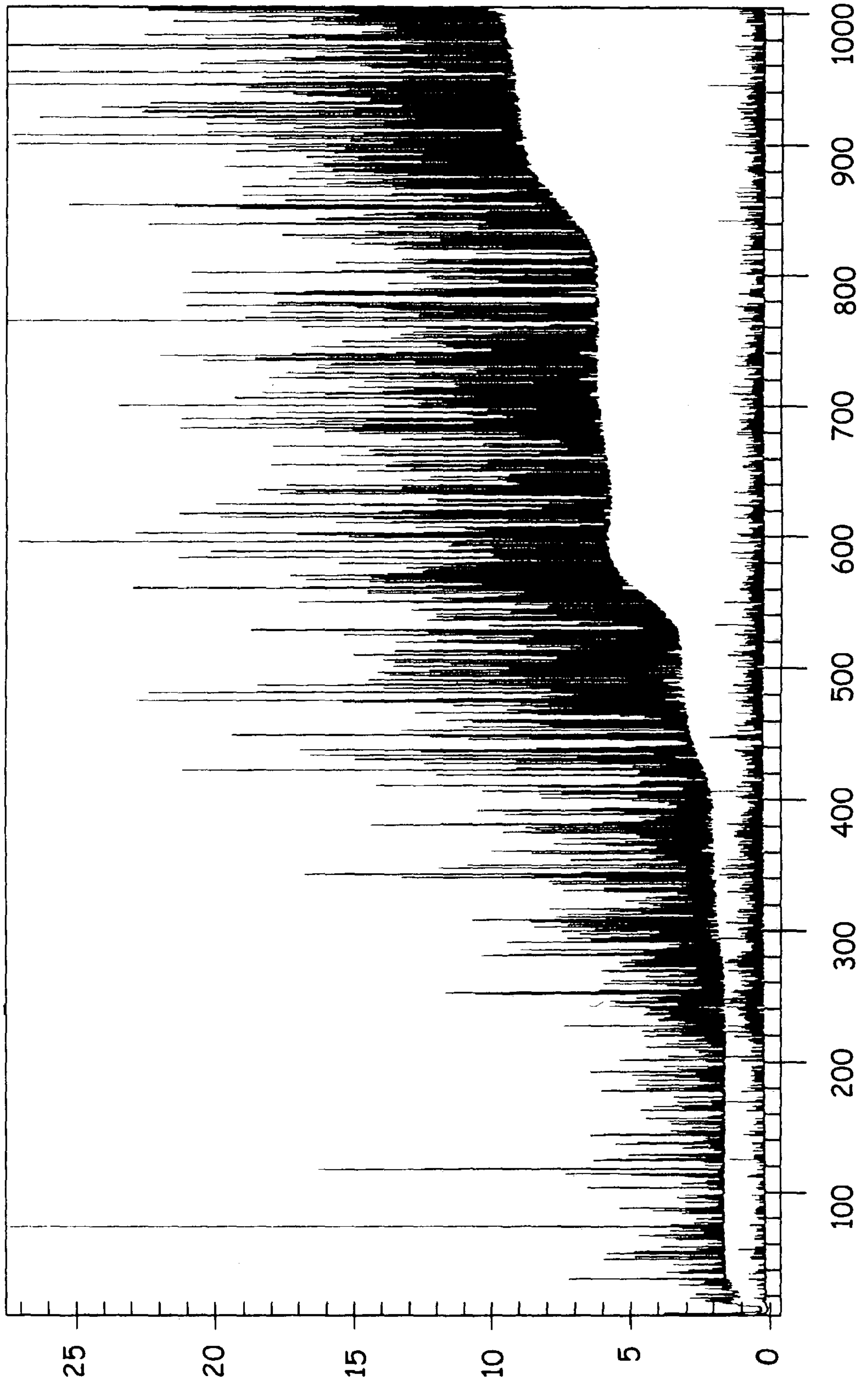
FIG. 8 illustrates a repeat of the experiment shown in FIG. 6, under slightly different assay conditions.
Figure 9:
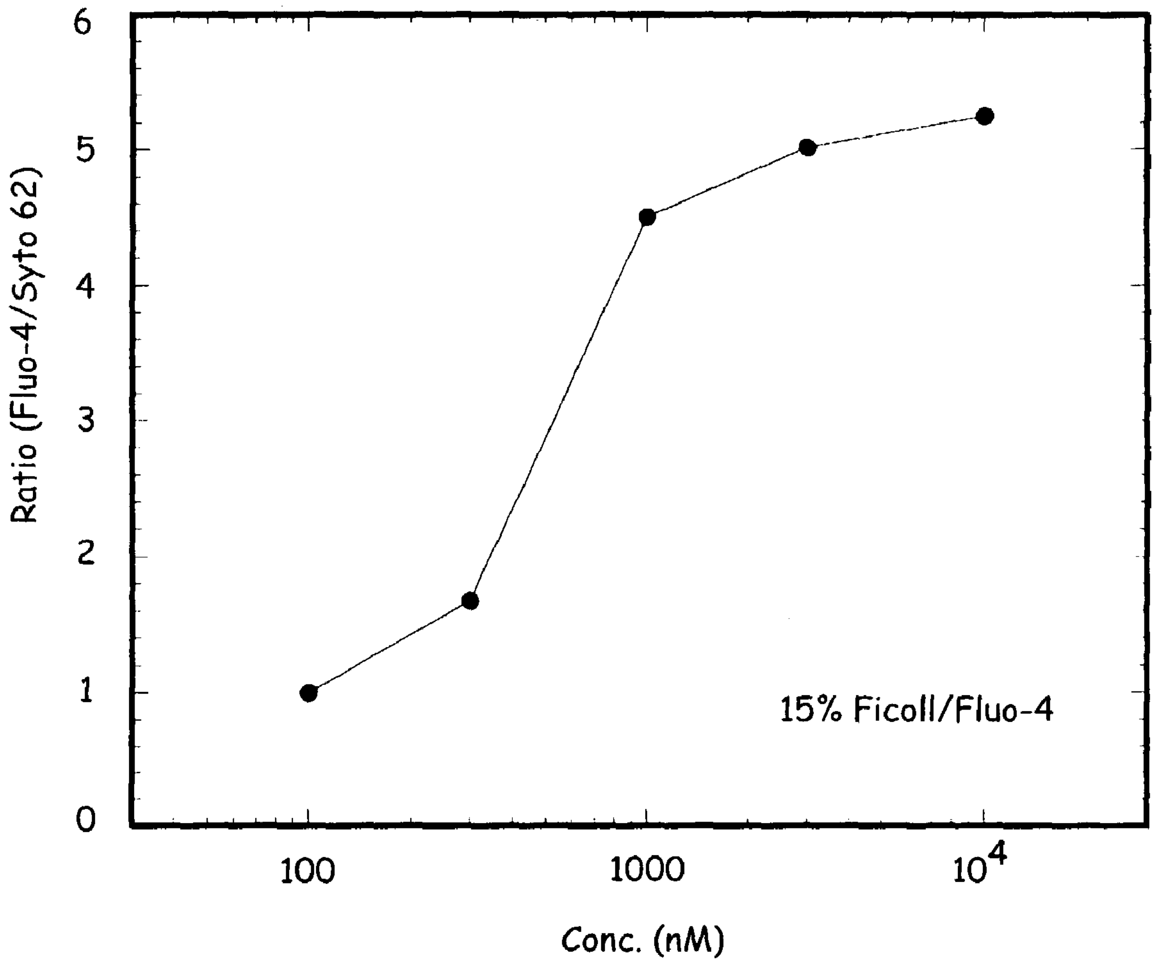
FIG. 9 illustrates a dose response curve generated from the data shown in FIG. 7.

In order to monitor the stepwise increase of each UTP reagent solution, an additional marker solution, BODIPY-arginine, was added to the reagent reservoirs 110-116. The raw data from the assay are shown in FIG. 6. As can be seen, the baseline for the detected response (upper data set) increases in a stepwise fashion, as a result of the added BODIPY-arginine dye. In addition, the signals from each cell, the peaks increase discernibly in size with each stepwise addition of the UTP reagent. FIG. 7 illustrates a dose response curve calculated from the data shown in FIG. 6. Briefly, the slope of calcium signal (response) vs. Syto 62 signal (cell number) was calculated for each UTP concentration. That slope was then plotted against the log[UTP] to obtain the dose response curve shown in FIG. 7. The assay was repeated using Cell Buffer containing 15% Ficoll. The raw data from this experiment are shown in FIG. 8 with the dose response curve shown in FIG. 9.

As can be seen from FIGS. 6 through 9, the methods and devices described in the present application provide an effective and simple method of performing iterative reaction operations in microfluidic systems, such as the determination of a dose response curve, as exemplified herein.

Unless otherwise specifically noted, all concentration values provided herein refer to the concentration of a given component as that component was added to a mixture or solution independent of any conversion, dissociation, reaction of that component to a alter the component or transform that component into one or more different species once added to the mixture or solution. In addition, any order that is given to method and/or process steps described herein is primarily for ease of description and does not limit such methods and/or processes to the order of steps as described, unless an order of steps is plainly clear from the express text or from the context of the description.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of performing successive reactions in a microfluidic device, comprising:

providing a microfluidic device comprising a reaction zone disposed within the microfluidic device, wherein the reaction zone is in fluid communication with a source of first reagent through a first fluid path, with a source of second reagent through a second fluid path, and with a source of third reagent through a third fluid path, wherein the second and third fluid paths are configured to deliver the second reagent to the reaction zone prior to the third reagent;

applying the same constant driving force across each of the first fluid path, the second fluid path, and the third fluid path to flow the first reagent through the reaction zone, introduce the second reagent into the reaction zone causing a first reaction between the first reagent and the second reagent, and subsequently introduce the third reagent into the reaction zone to cause a second reaction between the first reagent and the third reagent;

detecting an effect of the first reaction as a reactant or product of the first reaction flows through detection zone; and detecting an effect of the second reaction as a reactant or product of the second reaction flows through the detection zone.

2. The method of claim 1, wherein the fluid communication between the reaction zone and the first, second and third reagent sources is provided by a first channel fluidly connecting the source of first reagent and the reaction zone, a second channel fluidly connecting the source of second reagent and the reaction zone, and a third channel fluidly connecting the source of third reagent and the reaction zone.

3. The method of claim 2, wherein the second channel and the third channel intersect the reaction zone at a single point.

4. The method of claim 2, wherein the second channel and the third channel intersect the reaction zone at separate points.

5. The method of claim 2, wherein the third channel is longer than the second channel.

6. The method of claim 2, wherein the cross sectional area of the second channel is larger than the cross sectional area of the third channel.

7. The method of claim 6, wherein the aspect ratio of the second and third channels is greater than about 5.

8. The method of claim 1, wherein the driving force is a vacuum.

9. The method of claim 8, wherein the vacuum is applied to the reaction zone.

10. A method of performing successive reactions in a microfluidic device, comprising:

providing a microfluidic device comprising a reaction zone disposed within the microfluidic device, wherein the reaction zone is in fluid communication with a source of first reagent through a first fluid path, with a source of second reagent through a second fluid path, and with a source of third reagent through a third fluid path, wherein the second and third fluid paths are configured to deliver the second reagent to the reaction zone prior to the third reagent;

applying the same constant driving force across each of the first fluid path, the second fluid path and the third fluid path to flow the first reagent through the reaction zone, introduce the second reagent into the reaction zone causing a first reaction between the first reagent and the second reagent to produce a first product, and subsequently introduce the third reagent into the reaction zone to cause a second reaction between the first product and the third reagent; and detecting an effect of the second reaction as a reactant or product of the second reaction flows through detection zone.

11. The method of claim 10, wherein the fluid communication between the reaction zone and the first, second and third reagent sources is provided by a first channel fluidly connecting the source of first reagent and the reaction zone, a second channel fluidly connecting the source of second reagent and the reaction zone, and a third channel fluidly connecting the source of third reagent and the reaction zone.

12. The method of claim 11, wherein the second channel and the third channel intersect the reaction zone at a single point.

13. The method of claim 11, wherein the second channel and the third channel intersect the reaction zone at separate points.

14. The method of claim 11, wherein the third channel is longer than the second channel.

15. The method of claim 11, wherein the cross sectional area of the second channel is larger than the cross sectional area of the third channel.

16. The method of claim 15, wherein the aspect ratio of the second and third channels is greater than about 5.

17. The method of claim 10, wherein the driving force is a vacuum.

18. The method of claim 17, wherein the vacuum is applied to the reaction zone.

19. A method of determining a dose response of a first reagent on a biochemical system, comprising:

providing a microfluidic device comprising a body structure, a reaction zone disposed within the body structure, the reaction zone being fluidly connected to a first reagent source through a first fluid path, to a second reagent source through a second fluid path, and to a third reagent source through a third fluid path, the first reagent source comprising a first reagent, the second reagent source comprising a second reagent at a first concentration, and the third reagent source comprising the second reagent at a second concentration greater than the first concentration, wherein the second and third fluid paths are configured to deliver the second concentration to the reaction zone subsequent to delivering the first concentration of the second reagent to the reaction zone under the application of the same constant driving force across each of the fluid paths;

detecting an effect of each of the first concentration of the second reagent and the second concentration of the second reagent on the first reagent within the reaction zone as the reactants or products flow though a detection zone; and generating a dose response curve from the detected effect.

20. The method of claim 19, wherein the first fluid path comprises a first channel, the second fluid path comprises a second channel, and the third fluid path comprises a third channel.

21. The method of claim 20, wherein the second channel and the third channel intersect the reaction zone at a single point.

22. The method of claim 20, wherein the second channel and the third channel intersect the reaction zone at separate points.

23. The method of claim 20, wherein the third channel is longer than the second channel.

24. The method of claim 20, wherein the cross sectional area of the second channel is larger than the cross sectional area of the third channel.

25. The method of claim 24, wherein the aspect ratio of the second and third channels is greater than about 5.

26. The method of claim 19, wherein a vacuum is applied to the reaction zone.

* * * * *